United States Patent
Myllykangas et al.

(10) Patent No.: US 11,241,181 B2
(45) Date of Patent: Feb. 8, 2022

(54) BIO-SIGNAL MEASUREMENT APPARATUS, DOCKING APPARATUS AND METHODS OF THEIR COUPLING

(71) Applicant: BITTIUM BIOSIGNALS OY, Kuopio (FI)

(72) Inventors: Juha Myllykangas, Kuopio (FI); Sami Hynynen, Kuopio (FI)

(73) Assignee: BITTIUM BIOSIGNALS OY, Kuopio (FI)

( * ) Notice: Subject to any disclaimer, the term of this patent is extended or adjusted under 35 U.S.C. 154(b) by 299 days.

(21) Appl. No.: 16/559,763

(22) Filed: Sep. 4, 2019

(65) Prior Publication Data

US 2021/0059546 A1  Mar. 4, 2021

(51) Int. Cl.
*A61B 5/24* (2021.01)
*H01R 33/72* (2006.01)
(Continued)

(52) U.S. Cl.
CPC .............. *A61B 5/24* (2021.01); *H01R 33/72* (2013.01); *H01R 33/945* (2013.01);
(Continued)

(58) Field of Classification Search
CPC ........... A61B 5/24; A61B 5/318; A61B 5/369; A61B 5/389; A61B 5/398; H01R 33/72;
(Continued)

(56) References Cited

U.S. PATENT DOCUMENTS

| 6,524,240 B1 * | 2/2003 | Thede ................... A61B 5/021 128/897 |
| 2002/0137997 A1 * | 9/2002 | Mastrototaro ....... A61B 5/6849 600/345 |

(Continued)

FOREIGN PATENT DOCUMENTS

| EP | 3 586 734 | 1/2020 |
| WO | WO 2018/0155386 | 8/2018 |

*Primary Examiner* — Christopher A Flory
(74) *Attorney, Agent, or Firm* — Nixon & Vanderhye PC (57) ABSTRACT

A bio-signal measurement apparatus comprises tool-less connectors, coupling targets, a controllable coupling selection arrangement, and a control arrangement. The tool-less connectors are for an electric contact with a separate docking apparatus or an electrode arrangement. The coupling targets include a battery and a data communication unit that performs electrically a plug-and-play data transfer with the separate docking apparatus. The tool-less connectors, the number of which is three, are electrically coupled with the controllable coupling selection arrangement, which electrically couples all the tool-less connectors with only one of the coupling targets at a time in response to control from the control arrangement. The battery receives electricity from the tool-less connectors for charging the battery through the electric coupling caused by the coupling selection arrangement under control of the control arrangement during a first time window when the bio-signal measurement apparatus is connected with the docking apparatus. The data communication unit sends and/or receives data through the tool-less connectors using the plug-and-play data transfer based on (Continued)

the electric coupling caused by the coupling selection arrangement under control of the control arrangement during a second time window when the bio-signal measurement apparatus is connected with the docking apparatus.

15 Claims, 4 Drawing Sheets (51) Int. Cl.
H01R 33/945 (2006.01)
H02J 7/00 (2006.01)
A61B 5/398 (2021.01)
A61B 5/369 (2021.01)
A61B 5/318 (2021.01)
A61B 5/389 (2021.01)

(52) U.S. Cl.
CPC ............ H02J 7/0045 (2013.01); A61B 5/318 (2021.01); A61B 5/369 (2021.01); A61B 5/389 (2021.01); A61B 5/398 (2021.01); A61B 2560/0456 (2013.01); A61B 2562/227 (2013.01); H01R 2201/20 (2013.01)

(58) Field of Classification Search
CPC .... H01R 33/945; H02J 7/0044; H02J 7/0045; H04W 12/043
See application file for complete search history.

(56) References Cited

U.S. PATENT DOCUMENTS

| | | | | |
|---|---|---|---|---|
| 2008/0057779 A1* | 3/2008 | Mastrototaro | ..... | H01R 13/6683 439/502 |
| 2011/0125040 A1* | 5/2011 | Crawford | ............... | A61B 5/335 600/509 |
| 2011/0208076 A1* | 8/2011 | Fong | ................... | A61B 5/0205 600/509 |
| 2011/0273839 A1* | 11/2011 | Villegas | ............... | A61B 5/0004 361/679.41 |
| 2012/0316418 A1 | 12/2012 | Kilsgaard et al. | | |
| 2013/0253334 A1* | 9/2013 | Al-Ali | .................. | A61B 5/0022 600/476 |
| 2014/0100468 A1 | 4/2014 | Yu et al. | | |
| 2014/0371611 A1* | 12/2014 | Kim | ...................... | A61B 5/0006 600/509 |
| 2015/0112151 A1* | 4/2015 | Muhsin | ................. | A61B 5/0013 600/301 |
| 2015/0138704 A1* | 5/2015 | Thompson | ............ | G06F 1/1632 361/679.4 |
| 2015/0220476 A1* | 8/2015 | Kojima | ................. | H04W 12/06 710/106 |
| 2015/0257647 A1* | 9/2015 | Buck | .................... | A61B 5/6804 600/388 |
| 2015/0359429 A1* | 12/2015 | Al-Ali | .................. | A61B 5/6826 600/476 |
| 2016/0056647 A1* | 2/2016 | Choi | ..................... | H02J 7/0045 320/107 |
| 2016/0228060 A1* | 8/2016 | Mazar | .................. | A61B 5/6833 |
| 2016/0262671 A1* | 9/2016 | Villegas | ................ | A61B 5/1495 |
| 2017/0170670 A1* | 6/2017 | Shimura | ................ | G06F 1/1626 |
| 2018/0102606 A1* | 4/2018 | Tham | ................. | H01R 13/6205 |
| 2018/0206729 A1* | 7/2018 | Wang | ................... | A61B 5/0008 |
| 2019/0117983 A1* | 4/2019 | Andrews | .............. | A61N 1/3975 |
| 2019/0117984 A1* | 4/2019 | Andrews | .............. | H02J 7/0063 |
| 2019/0117987 A1* | 4/2019 | Beyer | .................... | H01R 33/74 |
| 2019/0117988 A1* | 4/2019 | Beyer | .................... | A61N 1/025 |
| 2019/0117989 A1* | 4/2019 | Andrews | .............. | H02J 7/0047 |
| 2019/0175019 A1* | 6/2019 | Al-Ali | .................... | G16H 10/60 |
| 2019/0231241 A1* | 8/2019 | Al-Ali | .................. | A61B 5/0022 |
| 2019/0239824 A1* | 8/2019 | Muhsin | ............... | A61B 5/02055 |
| 2019/0386498 A1* | 12/2019 | Higgins | ................ | H02J 7/0021 |
| 2020/0321793 A1* | 10/2020 | Al-Ali | ...................... | A61B 5/01 |
| 2020/0350728 A1* | 11/2020 | Patton | ................... | H02J 7/0045 |
| 2020/0360708 A1* | 11/2020 | Andrews | ............... | H01R 33/90 |
| 2021/0128042 A1* | 5/2021 | Herberger | ................ | A61B 5/25 |
| 2021/0194178 A1* | 6/2021 | Tham | .................... | H02J 7/0029 |
| 2021/0330224 A1* | 10/2021 | Al-Ali | ................... | A61B 5/7445 |
| 2021/0344140 A1* | 11/2021 | Patton | ..................... | H02J 7/345 |

* cited by examiner

BIO-SIGNAL MEASUREMENT APPARATUS, DOCKING APPARATUS AND METHODS OF THEIR COUPLING

FIELD

The invention relates to a bio-signal measurement apparatus, docking apparatus and methods of their coupling.

BACKGROUND

Electronic devices are used to measure bio-signals such as ECG (ElectroCardioGram) and EEG (ElectroEncephaloGram. Typically, such electronic devices can be connected with another device using a standard USB connector for a data transfer and charging. However, the USB connector is not an ideal connector. For example, dust and moisture may have unfavourable effects in an electric coupling based on the USB connectors in addition to a complexity of the connector structure.

Hence, there is a need to improve the bio-signal measurement systems and methods.

BRIEF DESCRIPTION

The present invention seeks to provide an improvement in the bio-signal measurement system.

The invention is defined by the independent claims. Embodiments are defined in the dependent claims.

LIST OF DRAWINGS

Example embodiments of the present invention are described below, by way of example only, with reference to the accompanying drawings, in which.

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

Figure 1:
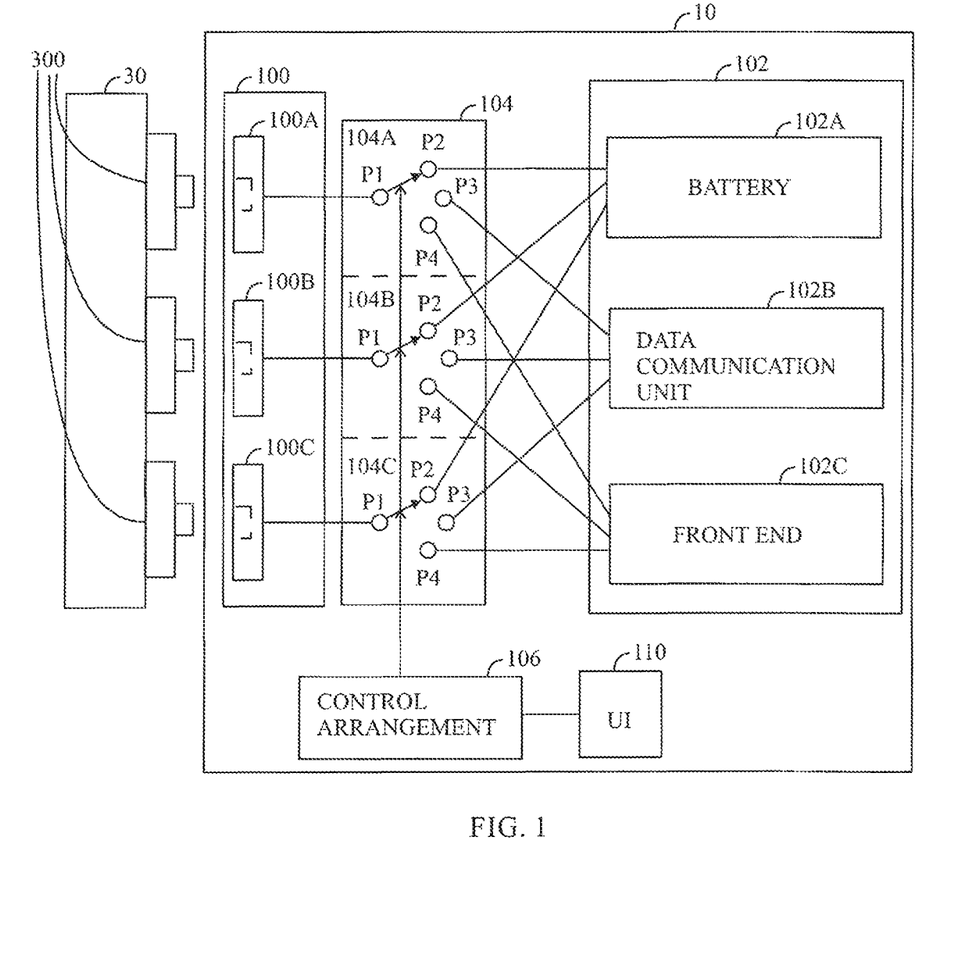
FIG. 1 illustrates an example of a block diagram of a bio-signal measurement apparatus.

FIG. 1 illustrates an example of a block diagram of a bio-signal measurement apparatus 10, which may be an electronic device converting an analog bio-signal it receives from an electrode arrangement 30 (see also FIG. 3) to a digital bio-signal. The bio-signal measurement apparatus 10 may also filter the bio-signal in an analog or in a digital form. Additionally or alternatively, the bio-signal measurement apparatus 10 may perform data processing of the bio-signal, and it may also store data of the bio-signal and/or a result of its processing. The bio-signal may be related to heart rate variability, electrocardiogram, electromyogram, electroencephalogram or the like for example. The bio-signal measurement apparatus 10, a separate docking apparatus 20 (see FIG. 2) and the electrode arrangement 30 together can be considered to form a bio-signal measurement system.

The bio-signal measurement apparatus 10 comprises tool-less connectors 100A, 100B, 100C, which are for an electric contact with and the electrode arrangement 30 during a measurement of the bio-signal and the separate docking apparatus 20 during data communication and/or charging. The number of the tool-less connectors 100A, 100B, 100C of the bio-signal measurement apparatus 10 for a full data communication and/or charging is three. That is, in an embodiment the number of the tool-less connectors 100A, 100B, 100C is no more or no less than three.

The tool-less connectors 100A, 100B, 100C of the bio-signal measurement apparatus 10 are separate from each other. That is, they have a physical distance therebetween. Each of the tool-less connectors 100A, 100B, 100C, the tool-less counter connectors 200A, 200B, 200C and connector units 300 is made of electrically conductive material. The material may be metal or electrically conductive polymer. The tool-less connectors 100A, 100B, 100C are repeatedly connectable to and disconnectable from their counter connectors 200A, 200B, 200C of the docking apparatus 20 and the connector units 300 of the electrode arrangement 30. The connection between the tool-less connectors 100A, 100B, 100C and the counter connectors 200A, 200B, 200C and the connection between the tool-less connectors 100A, 100B, 100C and the connector units 300 being electrical and/or galvanic. The connection between the tool-less connectors 100A, 100B, 100C and the tool-less counter connectors 200A, 200B, 200C can be performed one by one. That is, a connection between one of the tool-less connectors 100A, 100B, 100C and one of the tool-less counter connectors 200A, 200B, 200C does not lead to a connection between any other tool-less connectors 100A, 100B, 100C and the tool-less counter connectors 200A, 200B, 200C.

In an embodiment, a height of the tool-less connectors 100A, 100B, 100C may be less than about 3 mm, for example. In an embodiment, a height of the tool-less connectors 100A, 100B, 100C may be less than about 2 mm, for example. In an embodiment, a height of the tool-less connectors 100A, 100B, 100C may be less than about 1 mm, for example. Said height may be measured in a direction parallel to a force used for a connection and a disconnection between a tool-less connector 100A, 100B, 100C and a tool-less counter connector 200A, 200B, 200C or a disconnection between a tool-less connector 100A, 100B, 100C and a connector unit 300.

A tool-less connectors 100A, 100B, 100C and tool-less counter connectors 200A, 200B, 200C can be connected to and disconnected from each other using a finger force applied thereto by fingers of a person. Correspondingly, tool-less connectors 100A, 100B, 100C and connector units 300 can be connected to and disconnected from each other using a finger force applied thereto by fingers of a person. That is why it is question of tool-less connectors and tool-less counter connectors.

A pair of a tool-less connector 100A, 100B, 100C and a tool-less counter connector 200A, 200B, 200C may be realized as a snap-together-fastener pair. Correspondingly, a pair of a tool-less connector 100A, 100B, 100C and a connector unit 300 may be realized as a snap-together-fastener pair.

The coupling targets 102 of the bio-signal measurement apparatus 10 include a battery 102A and a data communication unit 102B. The data communication unit 102B performs electrically a plug-and-play data transfer with the separate docking apparatus 20. The data communication unit 102B also records the bio-signal received from the electrode arrangement 30 when they are connected with each other through the tool-less connectors 100A, 100B, 100C and the connector units 300 of the electrode arrangement 30. The recording may start and end automatically or under manual control of a user through a user interface 110. The communication unit 102B, while having a connection through the tool-less connectors 100A, 100B, 100C and the counter connectors 200A, 200B, 200C between the bio-signal measurement apparatus 10 and the docking apparatus 20, may provide plug-and-play capability, which, in turn, may be realized as a plug-and-play protocol. The data communication unit 102B may thus initiate the plug-and-play data transfer or the data communication unit 102B may accept or allow the plug-and-play data transfer which is initiated by the separate docking apparatus 20.

The data communication unit 102B may comprise a USB memory component (USB=Universal Serial Bus), for example. A standard USB connector has four pins such that a first pin is for the positive operational voltage of the bus, a second pin and a third pin carry data (+D, −D) (in a differential form), and a fourth pin is for ground. The operational voltage may be +5V. However, the data transfer of the USB memory of the data communication unit 102B is arranged using only three pins. Namely, two of the tool-less connectors 100A, 100B, 100C carry the differential data signalling (+D, −D) and one of the tool-less connectors 100A, 100B, 100C is ground. The positive operational voltage is not needed and not used for the data transfer. The plug-and-play capability, which is an inbuilt functionality of the USB, allows switching between components such as coupling targets 102 and coupling objects 202 without restarting the bio-signal measurement system.

Figure 2:
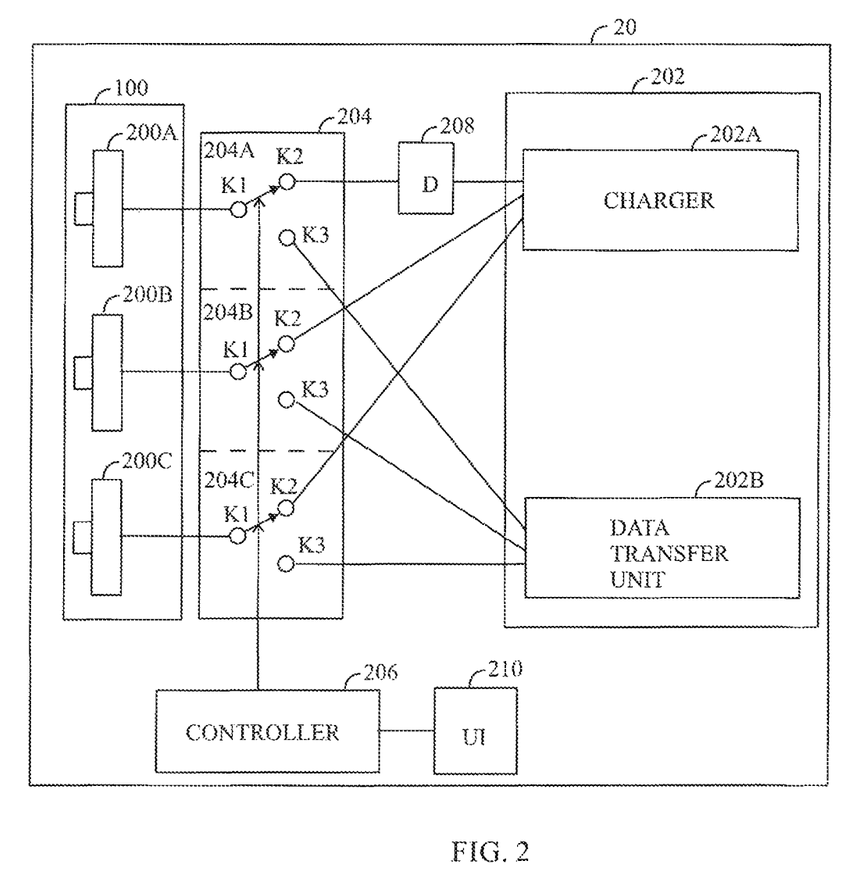
FIG. 2 illustrates an example of a block diagram of a docking apparatus.

The plug-and-play protocol allows the docking apparatus 20 or a counterpart of the bio-signal measurement apparatus 10 to find the data communication unit 102B automatically in the bio-signal measurement system or allows the data communication unit 102B to find a counterpart i.e. a data transfer unit 202B of the docking apparatus 20, when the bio-signal measurement apparatus 10 and the docking apparatus 20 are connected together, without configuration and/or manual setting.

The data communication unit 102B may store the bio-signal during a measurement, and the stored bio-signal may be transferred to the docking apparatus 20 after the bio-signal measurement is completed, for example.

The tool-less connectors 100A, 100B, 100C are electrically coupled with a controllable coupling selection arrangement 104, which may be a switch or a demultiplexer that in a selectable manner forms an electrical coupling between one pin P1 of one side and one of a plurality of pins P2, P3, P4 of another side. The controllable coupling selection arrangement 104, in turn, electrically couples all the tool-less connectors 100A, 100B, 100C with only one of the coupling targets 102 at a time in response to control from the control arrangement 106. The coupling may last for a predetermined portion of time. The control arrangement 106 can form different controls that it outputs to the controllable selection arrangement 104 at different moments. When a present control differs from a previous control, the controllable coupling selection arrangement 104 may switch the coupling of the tool-less connectors 100A, 100B, 100C from one coupling target 102A, 102B, 102C to another. The controllable selection arrangement 104 may switch between the coupling targets 102 in a repeated manner under control of the control arrangement 106. All the tool-less connectors 100A, 100B, 100C together are coupled with one of the targets 102 such that any pair of the tool-less connectors 100A, 100B, 100C is coupled with the same target 102 at any moment. The coupling, in turn, is performed simultaneously for all the tool-less connectors 100A, 100B, 100C.

When the bio-signal measurement apparatus 10 is connected with the separate docking apparatus 20 using the tool-less connectors 100A, 100B, 100C, the battery 102A may receive electricity from the tool-less connectors 100A, 100B, 100C, which may receive the electricity from the docking apparatus 20, for charging the battery 102A during a first time window. The electricity can flow through the electric coupling between the tool-less connectors 100A, 100B, 100C and the battery 102A, the coupling being caused by the coupling selection arrangement 104 under control of the control arrangement 106.

When the bio-signal measurement apparatus 10 is connected with the separate docking apparatus 20 using the tool-less connectors 100A, 100B, 100C, the data communication unit 102B may send and/or receive data through the tool-less connectors 100A, 100B, 100C, which may transfer the data to or from the docking apparatus 20, using the plug-and-play data transfer during a second time window. In this manner, communication is possible between the separate docking apparatus 20 and the bio-signal measurement apparatus 10, and the battery 102A of the bio-signal measurement apparatus 10 can be charged using the charger 202A of the docking apparatus 20 during non-overlapping time windows.

Figure 3:
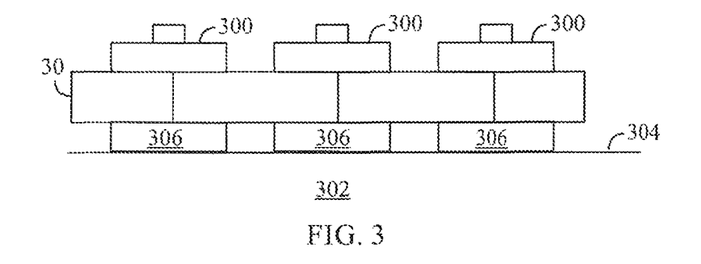
FIG. 3 illustrates an example of a block diagram of an electrode arrangement.

In an embodiment, the coupling targets 102 of the bio-signal measurement apparatus 10 may additionally comprise a front end 102C. The controllable coupling selection arrangement 104 may couple all the tool-less connectors 100A, 100B, 100C with the front end 102C for a third time window in response to the control from the control arrangement 106 for saving or storing a bio-signal outside the bio-signal measurement apparatus 10. Then a coupling between the tool-less connectors 100A, 100B, 100C and connector units 300 of the electrode arrangement 30 is formed. The electrode arrangement 30, an example of which is illustrated in FIG. 3 in addition to FIG. 1, is in contact with skin 304 of a mammal 302 in order to measure the bio-signal. The connector units 300 of the electrode arrangement 30 and the tool-less connectors 100A, 100B, 100C fit each other for allowing electric connectivity.

The front end 102C may comprise at least one computer program and/or an electric circuit. The front end 102C may perform an analog-digital conversion if the coming bio-signal is in an analog form and/or filter the bio-signal. Additionally, the front end 102C may be used to protect the patient electrically. One or more protective resistor and/or protective impedance component may be used in the electrode arrangement 30, which may be disposable, or to the front end 102A, which is on during the measurement. Additionally or alternatively, at least one electric protection component may be for defibrillation protection.

In an embodiment, the control arrangement 106 may receive an input from a user for controlling the controllable coupling selection arrangement 104 in order to select one of the targets 102 for the tool-less connectors 100A, 100B, 100C. The input may be received from the user interface 110 or 210 of the bio-signal measurement apparatus 10 or the docking apparatus 20. The user interface 110 may comprise a key, a keyboard and/or a touch screen, for example, for performing the input.

In an embodiment, the control arrangement 106 may control the controllable coupling selection arrangement 104 to select a coupling between the battery 102A and the tool-less connectors 100A, 100B, 100C for the first time window in response to an initiation of an contact between the tool-less connectors 100A, 100B, 100C and tool-less counter connectors 200A, 200B, 200C of the separate docking apparatus 20. The control arrangement 106 may detect the initiation of the contact to the tool-less connectors 100A, 100B, 100C based on electric measurement related to the tool-less connectors 100A, 100B, 100C, for example. The measurement of the detection of the initiation of the contact is known, per se, to a person skilled in the art. In this manner, a probability that the battery 102A is charged before a later operation of the bio-signal measurement apparatus 10 on the electric power of the battery 102A partly or alone may be maximized.

In an embodiment, the battery 102A is charged to its maximum charge capacity during the first time window. That is, the duration of the first time window may depend on the time it takes for the battery 102A to become fully charged. The control arrangement 106 may detect or estimate the charging level of the battery 102A. The detection or the estimation of the charging level of the battery 102A, per se, may be performed in a known manner. The control arrangement 106 may end the charging of the battery 102A on the basis of the detected or estimated charging level of the battery 102A. In this manner, the control arrangement 106 may set a duration of the first time window.

In an embodiment, the control arrangement 106 may control the controllable selection arrangement 104 to switch from the coupling between the tool-less connectors 100A, 100B, 100C and the battery 102A to the coupling between the tool-less connectors 100A, 100B, 100C and the data communication unit 102B in response to the detection or the estimation of the maximum charge capacity of the battery 102A.

In an embodiment, the control arrangement 106 may control the controllable selection arrangement 104 to switch from the coupling between the tool-less connectors 100A, 100B, 100C and the battery 102A to the coupling between the tool-less connectors 100A, 100B, 100C and the front end 102C in response to the detection of the estimation of the maximum charge capacity of the battery 102A. The control arrangement 106 may cause the controllable coupling selection arrangement 104 to couple all the tool-less connectors 100A, 100B, 100C with the front end 102C for the third time window on the basis of a coupling between the tool-less connectors 100A, 100B, 100C and connector units 300 of an electrode arrangement 30. The control arrangement 106 may detect the coupling between tool-less connectors 100A, 100B, 100C and the connector units 300 of the electrode arrangement 30, per se, in a manner known to a person skilled in the art, or the control arrangement 106 may receive an input about the coupling between tool-less connectors 100A, 100B, 100C and the connector units 300 from a user.

FIG. 2 illustrates an example of a block diagram of a docking apparatus 20. The docking apparatus 20 comprises tool-less counter connectors 200A, 200B, 200C, which fit with the tool-less connectors 100A, 100B, 100C of the bio-signal measurement apparatus 10. The number of the tool-less counter connectors 200A, 200B, 200C is three, and they are for the coupling with the tool-less connectors 100A, 100B, 100C of the separate bio-signal measurement apparatus 10. The tool-less counter connectors 200A, 200B, 200C of the docking apparatus 20 are separate from each other in a similar manner to the tool-less connectors 100A, 100B, 100C.

A height of the counter connectors 200A, 200B, 200C may be about the same as a height suitable for or in an embodiment of the tool-less connectors 100A, 100B, 100C.

Coupling objects 202 of the docking apparatus 20 include a charger 202A and the data transfer unit 202B. The data transfer unit 202B performs electrically a plug-and-play data transfer with the separate measurement apparatus 10.

The data transfer unit 202B may comprise a USB memory component (USB=Universal Serial Bus), for example, which is similar to the data communication unit 102B. The standard USB connector has four pins such that a first pin is for the positive operational voltage of the bus, a second pin and a third pin carry data (+D, −D), and a fourth pin is for ground. The operational voltage may be +5V. However, the data transfer of a USB memory of the data transfer unit 202B is arranged using only three pins. Namely, two of the tool-less counter connectors 200A, 200B, 200C carry the data (+D, −D) and one of the tool-less counter connectors 200A, 200B, 200C is ground. The positive operational voltage is not needed for the data transfer.

The docking apparatus 20 with its controller 206 allows the data transfer to and from the bio-signal measurement apparatus 10 by changing switching positions of the controllable switch arrangement 204. Then the plug-and-play operation may be realized by switching the ground open and closed.

The data transfer unit 202B may comprise a standard USB connector for a connection with an external device.

When the docking apparatus 20 is connected with an external computer, for example, through a standard USB-connection using the data transfer unit 202B, D+, D− and ground of the data transfer unit 202B of the docking apparatus 20 are coupled with the external device. Then an internal VBUS-line of the external device, which is the positive operational voltage of the standard USB-connector, may be temporally switched on by a processor of the external device for the external device to observe a change in a state of the USB-connection, which in turn allows automatic handshaking and communication through the USB-connection between the docking apparatus 20 and the external device.

Either of the data communication unit 102B or the data transfer unit 202B may provide plug-and-play capability for the data transfer therebetween such that either of the data communication unit 102B or the data transfer unit 202B initiates the data transfer automatically or through a manual input by a user using the user interface 110 of the bio-signal measurement apparatus 10 or the user interface 210 of the docking apparatus 20 without restarting the bio-signal measurement system.

In an embodiment, the data communication unit 102B may initiate the communication between the data communication unit 102B and the data transfer unit 202B.

In an embodiment, the data transfer unit 202B may initiate the plug-and-play data transfer or the data transfer unit 202B may accept or allow the plug-and-play data transfer which is initiated by the separate bio-signal measurement apparatus 10.

The data transfer unit 202B may connect wirelessly or in a wired manner also to a computer, a base station or a router. The data transfer unit 202B may transfer the data it receives to the computer, the base station or the router. The data transfer to the computer, the base station or the router may be simultaneous to the reception from the bio-signal measurement apparatus 10 or it may performed at different time with respect to the reception from the bio-signal measurement apparatus 10. The base station or the router may deliver the data transmitted for the data transfer unit 202B also to a data network, which may be local or global. The data network may be the Internet, for example. The data transfer to the computer, the base station or the router does not necessarily need specific drivers for the data transfer because the data transfer unit 102B is capable of using the plug-and-play protocol.

The tool-less counter connectors 200A, 200B, 200C are electrically coupled with the controllable switch arrangement 204, which electrically couples all the tool-less counter connectors 200A, 200B, 200C with only one of the coupling objects 202 at a time in response to control from a controller 206. This operation corresponds to that of the bio-signal measurement apparatus 10, although the battery 102A is replaced with the charger 202A.

The controllable switch arrangement 204 may be a switch or a demultiplexer that in a selectable manner forms an electrical coupling between one pin K1 of one side and one of a plurality of pins K2 and K3 of another side.

The charger 202A is enabled to feed electricity to the tool-less counter connectors 200A, 200B, 200C for charging a battery 102A of the separate measurement apparatus 10 during the first time window through the electric coupling caused by the switch arrangement 204. The data transfer unit 202B sends and/or receives data through the tool-less counter connectors 200A, 200B, 200C using the plug-and-play data transfer based on the electric coupling caused by the switch arrangement 204 under control of the controller 206 during the second time window.

In an embodiment, the docking apparatus 20 may additionally comprise an electric detector 208, which detects an electric parameter of the electricity fed by the charger 202A. The controller 206 may cause an action, if the electric parameter detected by the electric detector 208 has a value beyond a limit of a determined threshold range. For example, a short cut or a disconnection somewhere in the electric circuits of the bio-signal measurement apparatus 10 or the docking apparatus 20 may cause the electric parameter to become too high or too low. A value of the electric parameter may deviate from the limit of the determined threshold range because of moisture and or sweat. The electric detector 208 may detect electric current. A person skilled in the art is capable of setting the threshold range, per se.

In an embodiment, the controller 206 may cause at least one of the following actions: limit the electricity fed by the charger 202A, cut the electricity fed by the charger 202A, and an alarm. The alarm may be caused by a user interface 210 of the docking apparatus 20, for example. The alarm may be mechanical vibration, an audible sound and/or a visible signal that can be sensed by a person. The user interface 210 may comprise a mechanical vibrator, a visible radiation source, a screen and/or an acoustic signal source, for example, for outputting the alarm.

In an embodiment, the controller 206 may receive an input from a user for controlling the controllable switch arrangement 204 to select one of the coupling objects 202 for the coupling with the tool-less counter connectors 200A, 200B, 200C. The input may be received from the user interface 110 or 210 of the bio-signal measurement apparatus 10 or the docking apparatus 20. The user interface 210 may comprise a key, a keyboard and/or a touch screen, for example, for performing the input.

In an embodiment, the controller 206 may control the controllable switch arrangement 204 to select a coupling between the charger 202A and the tool-less counter connectors 200A, 200B, 200C for the first time window in response to an initiation of an contact between the tool-less counter connectors 200A, 200B, 200C and tool-less connectors 100A, 100B, 100C of the separate measurement apparatus 10. In this manner, a probability that the battery 102A is properly charged for a later operation on the electric power of the battery 102A alone may be maximized.

In an embodiment, the controller 206 may measure or estimate a charging level of the battery 102B of the separate bio-signal measurement apparatus 10. The controller 206 may then control the charger 202A to continue feeding electricity until a detection by the controller 206 that the charging level, which is measured or estimated, and a determined charging level, which is available for the controller 206, are equal. The controller 206 may control the controllable switch arrangement 204 to select a coupling object 202 different from the charger 202A in response to said detection. The determined charging level may be used as a reference which the measured or estimated changing level should reach before stopping the charging.

FIG. 3 illustrates an example of the electrode arrangement 30. The electrodes 306 are, during a measurement, in physical touch with the skin 304 of the mammal, which may be a human being or an animal. The electrodes 306 receive the bio-signal from the skin 304 and pass it through conductors to connector units 300 of the electrode arrangement 30. The connector units 300 of the electrode arrangement 30 may be similar to the tool-less counter connectors 200A, 200B, 200C of the docking apparatus 20 for allowing an electrical connection with the tool-less connectors 100A, 100B, 100C.

Figure 4:
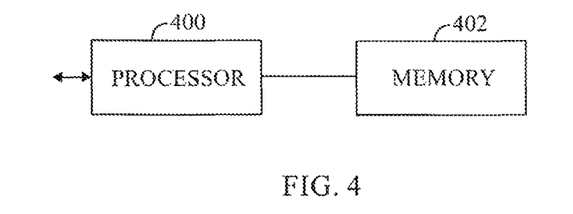
FIG. 4 illustrates an example of a block diagram of a control arrangement of the bio-signal measurement apparatus, which has at least one processor and at least one memory.

In an embodiment an example of which is illustrated in FIG. 4, the control arrangement 106 may comprise one or more processors 400 and one or more memories 402, which include computer program code. The one or more memories 402 and the computer program code configured to, with the one or more processors 400, cause the control arrangement 106 at least to control the controllable coupling selection arrangement 104 to electrically couple all the tool-less connectors 100A, 100B, 100C with only one of the coupling targets 102 at a time.

Figure 5:
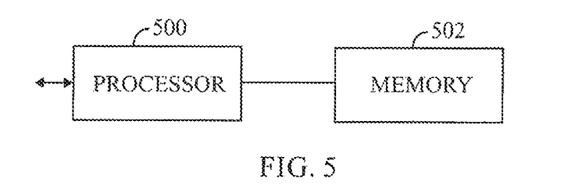
FIG. 5 illustrates an example of a block diagram of a controller of the docking apparatus, which has at least one processor and at least one memory.

In an embodiment an example of which is illustrated in FIG. 5, the controller 206, in a corresponding manner to the controlling arrangement 106, may comprise one or more processors 500 and one or more memories 502 including computer program code. The one or more memories 502 and the computer program code configured to, with the one or more processors 500, cause the controller 206 at least to control the controllable switch arrangement 204 to electrically couple all the tool-less connectors 200A, 200B, 200C with only one of the coupling objects 202 at a time.

This solution simplifies the device design and everyday use of the device. This solution may also lead to a minimized overall cost and maximized robustness of the apparatuses. A simple ECG (or EOG/EEG/EMG) apparatus that does not have the USB-connector or any unnecessary connector at all can be made. This yields a useable and cost-friendly bio-signal measurement apparatus system that can be made waterproof.

Figure 6:
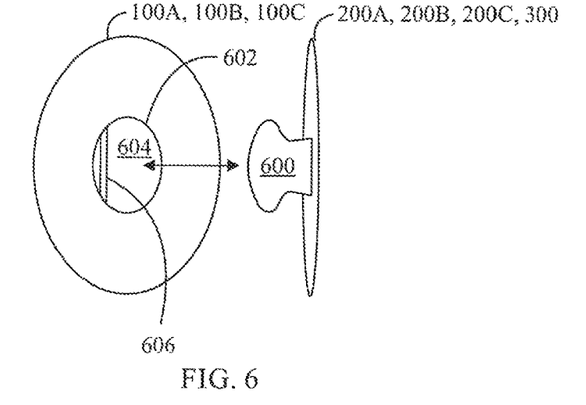
FIG. 6 illustrates an example of a tool-less connector and a corresponding tool-less counter connector.

A tool-less connector 100A, 100B, 100C and a corresponding tool-less counter connector 200A, 200B, 200C (and connector 300) form a pair of interlocking parts an example of which is shown in FIG. 6. In an embodiment, a tool-less counter connector 200A, 200B, 200C may have an extension 600 that fits into an aperture 602 of a hole 604 of the tool-less connector 100A, 100B, 100C. A size of the aperture 602 may be limited by at least one spring 606. When the extension 600 is pushed toward the aperture 602 the at least one spring 606 yields to the force widening the aperture 602, and the extension 600 enters the hole 604 through the aperture 602. Then the at least one spring 606 is in contact with a side of the extension 600 and applies a force against it, which causes a firm attachment between the tool-less counter connector 200A, 200B, 200C and the tool-less connector 100A, 100B, 100C based on friction. Additionally, the extension 600 may be larger at a top that first enters the hole 604 during a connection than a structure of the extensions 600 behind it for increasing the hold. The interlocking of one pair of the tool-less connectors 100A, 100B, 100C and the tool-less counter connectors 200A, 200B, 200C is independent from any other pair.

Figure 7:
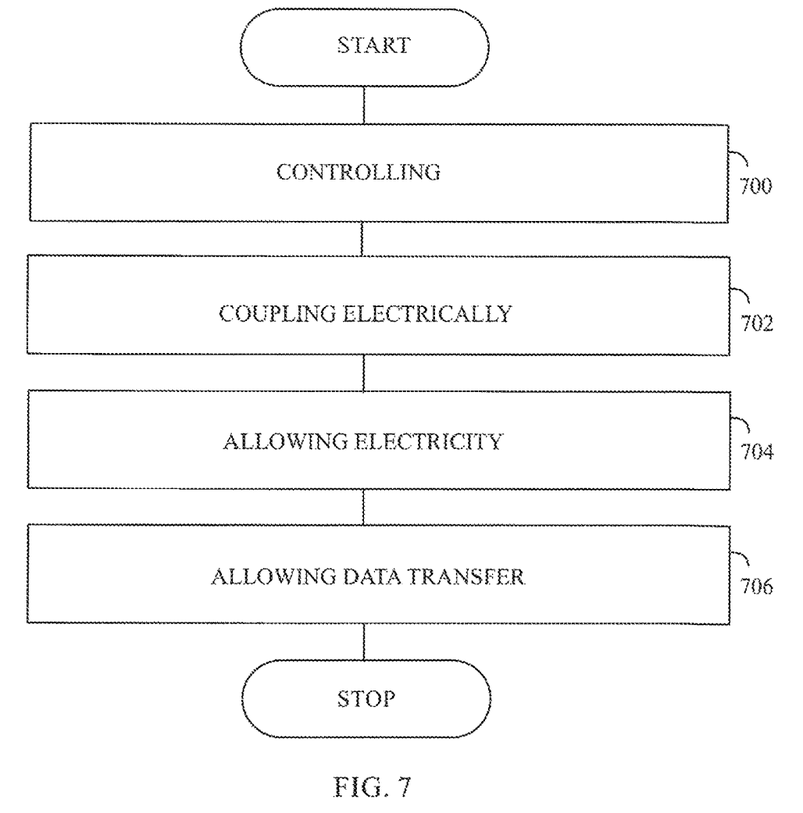
FIG. 7 illustrates of an example of a flow chart of an electric coupling method of the bio-signal measurement apparatus.

FIG. 7 is a flow chart of the electric coupling method of the bio-signal measurement apparatus 10. In step 700, a controllable coupling selection arrangement 104 of the bio-signal measurement apparatus 10 is controlled by a control arrangement 106.

In step 702, all tool-less connectors 100A, 100B, 100C of the bio-signal measurement apparatus 10 are coupled electrically, by the controllable coupling arrangement 104, with only one of the coupling targets 102 of the bio-signal measurement apparatus 10 at a time in response to control from the control arrangement 106 to the controllable coupling arrangement 104, the number of the tool-less connectors 100A, 100B, 100C being three, and the tool-less connectors 100A, 100B, 100C being for an electric contact with a separate docking apparatus 20.

In step 704, a reception of electricity is allowed from the tool-less connectors 100A, 100B, 100C to a battery 102A of the bio-signal measurement apparatus 10 for charging the battery 102A during a first time window when the bio-signal measurement apparatus 10 is connected with the docking apparatus 20.

In step 706, a transfer of data is allowed between a data communication unit 102B of the bio-signal measurement apparatus 10 and the tool-less connectors 100A, 100B, 100C using a plug-and-play data transfer during a second time window when the bio-signal measurement apparatus 10 is connected with the docking apparatus 20.

Figure 8:
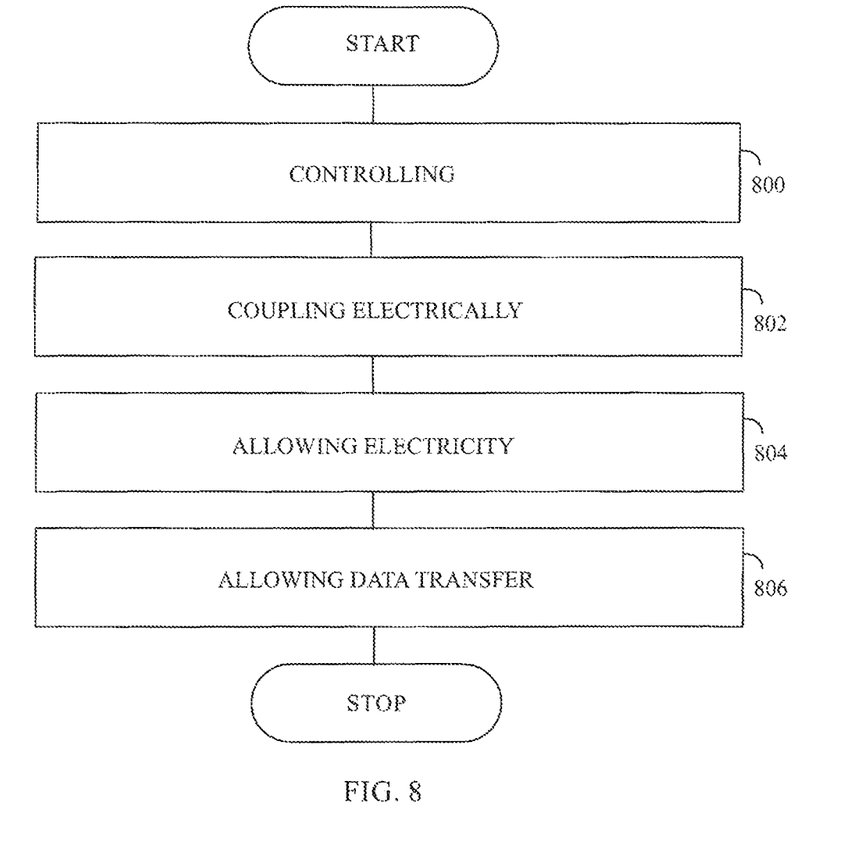
FIG. 8 illustrates of an example of a flow chart of an electric coupling of the docking apparatus.

FIG. 8 is a flow chart of the electric coupling method of docking apparatus 20. In step 800, a controllable switch arrangement 204 of the docking apparatus 20 is controlled by a controller 206.

In step 802, all tool-less counter connectors 200A, 200B, 200C of the docking apparatus 20 are coupled electrically, by the controlled switch arrangement 204, with only one of the coupling objects 202 of the docking apparatus 20 at a time in response to control from the controller 206 to the switch arrangement 204, the number of the tool-less counter connectors 200A, 200B, 200C being three, and the tool-less counter connectors 200A, 200B, 200C being for an electric contact with a measurement apparatus 10.

In step 804, feed of electricity is allowed to the tool-less counter connectors 200A, 200B, 200C from a charger 202A of the docking apparatus 20 for charging a battery 102A of a bio-signal measurement apparatus 10 during a first time window.

In step 806, a transfer of data is allowed between a data transfer unit 202B of the docking apparatus 20 and the tool-less counter connectors 200A, 200B, 200C using a plug-and-play data transfer during a second time window.

The methods shown in FIGS. 7 and 8 may be implemented as a logic circuit solution or computer program. The computer program may be placed on a computer program distribution means for the distribution thereof. The computer program distribution means is readable by the data communication unit 102B or the data transfer unit 202B, and it encodes the computer program commands, carries out the actions.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

There is a need to have a waterproof simple ECG device with three measurement contacts, which could be used for charging and communication of a measured signal and device settings. The features in this application enable a solution to these multiple problems. With only three separate tool-less connectors and their counter connectors it is possible to realize an automatic data transfer, charging and a hold mechanism for a measurement of a bio-signal from a patient.

It will be obvious to a person skilled in the art that, as technology advances, the inventive concept can be implemented in various ways. The invention and its embodiments are not limited to the example embodiments described above but may vary within the scope of the claims.

What is claimed is:

1. A bio-signal measurement apparatus, wherein the bio-signal measurement apparatus comprises:
tool-less connectors, the number of which is three, for an electric contact with a separate docking apparatus or an electrode arrangement,
coupling targets, which include a battery and a data communication unit that is configured to perform electrically a plug-and-play data transfer with the separate docking apparatus,
a controllable coupling selection arrangement, and
a control arrangement; and the tool-less connectors are electrically coupled with the controllable coupling selection arrangement, which is configured to electrically couple all the tool-less connectors with only one of the coupling targets at a time in response to control from the control arrangement; and the battery is configured to receive electricity from the tool-less connectors for charging the battery through the electric coupling caused by the coupling selection arrangement under control of the control arrangement during a first time window when the bio-signal measurement apparatus is connected with the docking apparatus, and the data communication unit is configured to send and/or receive data through the tool-less connectors using the plug-and-play data transfer based on the electric coupling caused by the coupling selection arrangement under control of the control arrangement during a second time window when the bio-signal measurement apparatus is connected with the docking apparatus.

2. The bio-signal measurement apparatus of claim 1, wherein the coupling targets comprise additionally a front end, and the controllable coupling selection arrangement is configured to couple all the tool-less connectors with the front end for a third time window in response to the control from the control arrangement on the basis of a coupling between the tool-less connectors and connector units of an electrode arrangement that is in contact with skin of a mammal, the connector units of the electrode arrangement and the tool-less connectors being configured to fit each other.

3. The bio-signal measurement apparatus of claim 1, wherein the control arrangement is configured to receive an input from a user for controlling the controllable coupling selection arrangement to select one of the targets for the tool-less connectors.

4. The bio-signal measurement apparatus of claim 1, wherein the control arrangement is configured to control the controllable coupling selection arrangement to select a coupling between the battery and the tool-less connectors for the first time window in response to an initiation of an contact between the tool-less connectors and tool-less counter connectors of the separate docking apparatus.

5. The bio-signal measurement apparatus of claim 4, wherein the control arrangement is configured to detect or estimate a charging level of the battery; and the control arrangement is configured to end the charging of the battery on the basis of the detected or estimated charging level of the battery.

6. The bio-signal measurement apparatus of claim 1, wherein the control arrangement comprises
one or more processors; and
one or more memories including computer program code;
the one or more memories and the computer program code configured to, with the one or more processors, cause the control arrangement at least to control the controllable coupling selection arrangement to electrically couple all the tool-less connectors with only one of the coupling targets at a time.

7. A docking apparatus for a separate bio-signal measurement apparatus, wherein the docking apparatus comprises
tool-less counter connectors, the number of which is three, for a coupling with a separate bio-signal measurement apparatus, coupling objects, which include a charger and a data transfer unit that is configured to perform electrically a plug-and-play data transfer with the separate measurement apparatus;
a controllable switch arrangement,
a controller; and
the tool-less counter connectors are electrically coupled with the controllable switch arrangement, which is configured to electrically couple all the tool-less counter connectors with only of the coupling objects at a time in response to control from the controller; and
the charger is configured to feed electricity to the tool-less counter connectors for charging a battery of the separate measurement apparatus through the coupling caused by the switch arrangement under control of the controller during a first time window, and the data transfer unit is configured to send and/or receive data through the tool-less counter connectors using the plug-and-play data transfer based on the electric coupling caused by the switch arrangement under control of the controller during a second time window for a communication with the measurement apparatus.

8. The docking apparatus of claim 7, wherein the docking apparatus comprises additionally an electric detector configured to detect an electric parameter of the electricity fed by the charger, and the controller is configured to cause an action, if the electric parameter detected by the electric detector is beyond a limit of a determined threshold range.

9. The docking apparatus of claim 8, wherein the controller is configured to cause at least one of the following actions: limit the electricity fed by the charger, cut the electricity fed by the charger, and an alarm.

10. The docking apparatus of claim 7, wherein the controller is configured to receive an input from a user for controlling the controllable switch arrangement to select one of the coupling objects for the coupling with the tool-less counter connectors of the docking apparatus.

11. The docking apparatus of claim 7, wherein the controller is configured to control the controllable switch arrangement to select a coupling between the charger and the tool-less counter connectors for a first time window in response to an initiation of an contact between the tool-less counter connectors of the docking apparatus and tool-less connectors of the separate measurement apparatus.

12. The docking apparatus of claim 7, wherein the controller is configured to measure or estimate a charging level of the battery of the separate bio-signal measurement apparatus, and control the charger to continue feeding electricity until a detection by the controller that the charging level, which is measured or estimated, and a determined charging level available for the controller are equal; and the controller is configured to control the controllable switch arrangement to select a coupling object different from the charger in response to said detection.

13. The docking apparatus of claim 7, wherein the controller comprises
one or more processors; and
one or more memories including computer program code;
the one or more memories and the computer program code configured to, with the one or more processors, cause the controller at least to control the controllable switch arrangement to electrically couple all the tool-less connectors of the docking apparatus with only one of the coupling objects at a time.

14. An electric coupling method of a bio-signal measurement apparatus, the method comprising:

controlling, by a control arrangement, a controllable coupling selection arrangement of the bio-signal measurement apparatus;

coupling electrically, by the controllable coupling arrangement, all tool-less connectors of the bio-signal measurement apparatus with only one of the coupling targets of the bio-signal measurement apparatus at a time in response to control from the control arrangement to the controllable coupling arrangement, the number of the tool-less connectors being three, and the tool-less connectors being for an electric contact with a separate docking apparatus or an electrode arrangement;

allowing a reception of electricity from the tool-less connectors to a battery of the bio-signal measurement apparatus for charging the battery during a first time window when the bio-signal measurement apparatus is connected with the docking apparatus; and allowing a transfer of data between a data communication unit of the bio-signal measurement apparatus and the tool-less connectors using a plug-and-play data transfer during a second time window when the bio-signal measurement apparatus is connected with the docking apparatus.

15. An electric coupling method of a docking apparatus, the method comprising:

controlling, by a controller, a controllable switch arrangement of the docking apparatus;

coupling electrically, by a controlled switch arrangement, all tool-less counter connectors of the docking apparatus with only one of the coupling objects of the docking apparatus at a time in response to control from the controller to the switch arrangement, the number of the tool-less counter connectors of the docking apparatus being three, and the tool-less counter connectors of the docking apparatus being for an electric contact with a bio-signal measurement apparatus;

allowing feed of electricity to the tool-less counter connectors of the docking apparatus from a charger of the docking apparatus for charging a battery of the bio-signal measurement apparatus during a first time window when the docking apparatus is connected with the bio-signal measurement apparatus; and allowing a transfer of data between a data transfer unit of the docking apparatus and the tool-less counter connectors of the docking apparatus using a plug-and-play data transfer during a second time window for communicating with the bio-signal measurement apparatus.

* * * * *